US009161868B2

(12) United States Patent
Corbellini et al.

(10) Patent No.: US 9,161,868 B2
(45) Date of Patent: Oct. 20, 2015

(54) REMOVAL OF COLORED SUBSTANCES FROM AQUEOUS LIQUIDS

(75) Inventors: Francesca Corbellini, Dusseldorf (DE); Eckhard Purkner, Dusseldorf (DE); Elisabeth Baumgarten, Duisburg (DE); Hans Bouten, Geldern (DE); Arndt Scheidgen, Essen (DE); Franz Aschenbrenner, Kastl (DE); Doohong Kim, Singapore (SG); Priscilla Eng Choo Goh, Singapore (SG)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 259 days.

(21) Appl. No.: 13/387,157

(22) PCT Filed: Aug. 31, 2010

(86) PCT No.: PCT/IB2010/053911
§ 371 (c)(1), (2), (4) Date: May 7, 2012

(87) PCT Pub. No.: WO2011/027295
PCT Pub. Date: Mar. 10, 2011

(65) Prior Publication Data
US 2012/0215192 A1    Aug. 23, 2012

(30) Foreign Application Priority Data

Sep. 4, 2009 (DE) .......................... 10 2009 029 194

(51) Int. Cl.
*A61F 13/15*    (2006.01)
*A61F 13/47*    (2006.01)
(Continued)

(52) U.S. Cl.
CPC ....... *A61F 13/8405* (2013.01); *A61F 13/47263* (2013.01); *A61L 15/18* (2013.01); *A61L 15/42* (2013.01); *A61F 2013/8408* (2013.01); *A61F 2013/8497* (2013.01)

(58) Field of Classification Search
CPC ................... A61F 13/00063; A61F 13/51113; A61F 13/8405; A61F 2013/00914; A61F 2013/8408; A61F 2013/8426; A61L 15/18; A61L 15/46; A61L 2300/102
USPC .......................................................... 604/367
See application file for complete search history.

(56) References Cited

U.S. PATENT DOCUMENTS 2,236,529 A    4/1941    Epstein et al.
2,418,907 A *  4/1947    Schreiber ...................... 604/359
(Continued)

FOREIGN PATENT DOCUMENTS

CN    1616115 A *  5/2005
EP    0019371 A1    11/1980
(Continued)

OTHER PUBLICATIONS

Senczuk et al. Hydrophobic Interaction Chromatography in Dual Salt System Increases Protein Binding Capacity. Biotech. Bioeng. vol. 103, No. 5, Aug. 1, 2009. Published online Mar. 9, 2009 in Wiley InterScience (www.interscience.wiley.com).*

(Continued)

*Primary Examiner* — Lynne Anderson
*Assistant Examiner* — Kathryn E Ditmer
(74) *Attorney, Agent, or Firm* — Dority & Manning, P.A.

(57) ABSTRACT

The use of a decolorizing composition for removing colored substances from aqueous fluids (e.g., colored pigments, blood-containing fluids, etc.) is provided. The decolorizing composition contains one or more inorganic salts. In one embodiment, for example, the composition contains a mixture of sodium sulfate ($Na_2SO_4$) and monopotassium phosphate ($KH_2PO_4$). The decolorizing composition may be placed in fluid communication with an absorbent core, a liquid-permeable layer, or combinations thereof, in an absorbent article to help decolorize blood-containing fluids (e.g., menses) exuded from the body.

8 Claims, 3 Drawing Sheets

(51) Int. Cl.
 *A61F 13/84* (2006.01)
 *A61F 13/472* (2006.01)
 *A61L 15/18* (2006.01)
 *A61L 15/42* (2006.01)

(56) References Cited

U.S. PATENT DOCUMENTS

| | | | |
|---|---|---|---|
| 2,542,909 A | 2/1951 | De Wet | |
| 3,124,135 A | 3/1964 | Olson | |
| 3,287,222 A | 11/1966 | Larde et al. | |
| 3,338,992 A | 8/1967 | Kinney | |
| 3,341,394 A | 9/1967 | Kinney | |
| 3,347,236 A | 10/1967 | Torr | |
| 3,397,697 A | 8/1968 | Rickard | |
| 3,398,097 A | 8/1968 | Kersnar et al. | |
| 3,490,454 A | 1/1970 | Goldfarb et al. | |
| 3,502,538 A | 3/1970 | Petersen | |
| 3,502,763 A | 3/1970 | Hartmann et al. | |
| 3,542,615 A | 11/1970 | Dobo et al. | |
| 3,635,828 A | 1/1972 | Benjamin et al. | |
| 3,663,445 A | 5/1972 | Augustin et al. | |
| 3,692,618 A | 9/1972 | Dorschner et al. | |
| 3,783,872 A | 1/1974 | King | |
| 3,802,817 A | 4/1974 | Matsuki et al. | |
| 3,814,101 A | 6/1974 | Kozak | |
| 3,849,241 A | 11/1974 | Butin et al. | |
| 3,953,351 A | 4/1976 | Keller | |
| 3,979,318 A | 9/1976 | Tokiwa et al. | |
| 4,100,324 A | 7/1978 | Anderson et al. | |
| 4,190,563 A | 2/1980 | Bosley et al. | |
| 4,250,257 A | 2/1981 | Lee et al. | |
| 4,259,383 A | 3/1981 | Eggensperger et al. | |
| 4,288,225 A | 9/1981 | Roland et al. | |
| 4,340,563 A | 7/1982 | Appel et al. | |
| 4,357,939 A | 11/1982 | Jackson et al. | |
| 4,363,322 A | 12/1982 | Andersson | |
| 4,381,784 A | 5/1983 | Aberson et al. | |
| 4,431,560 A | 2/1984 | Lake et al. | |
| 4,532,232 A | 7/1985 | Larsson et al. | |
| 4,585,650 A | 4/1986 | Newberry, Jr. et al. | |
| 4,594,327 A | 6/1986 | Zuk | |
| 4,636,209 A | 1/1987 | Lassen | |
| 4,655,759 A | 4/1987 | Romans-Hess et al. | |
| 4,673,524 A | 6/1987 | Dean | |
| 4,693,713 A | 9/1987 | Chmelir et al. | |
| 4,773,423 A | 9/1988 | Hakky | |
| 4,798,603 A | 1/1989 | Meyer et al. | |
| 4,801,494 A | 1/1989 | Datta et al. | |
| 4,803,153 A | 2/1989 | Shibata et al. | |
| 4,847,089 A | 7/1989 | Kramer et al. | |
| 4,855,108 A | 8/1989 | Masuda et al. | |
| 4,886,512 A | 12/1989 | Damico et al. | |
| 4,892,534 A | 1/1990 | Datta et al. | |
| 4,908,026 A | 3/1990 | Sukiennik et al. | |
| 4,933,092 A | 6/1990 | Aunet et al. | |
| 5,009,716 A | 4/1991 | Gerson | |
| 5,037,412 A * | 8/1991 | Tanzer et al. | 604/359 |
| 5,064,541 A | 11/1991 | Jeng et al. | |
| 5,118,428 A | 6/1992 | Sand et al. | |
| 5,147,698 A | 9/1992 | Cole | |
| 5,223,284 A * | 6/1993 | Kulczycki et al. | 426/42 |
| 5,248,309 A | 9/1993 | Serbiak et al. | |
| 5,262,153 A | 11/1993 | Mishima et al. | |
| 5,281,208 A | 1/1994 | Thompson et al. | |
| 5,284,703 A | 2/1994 | Everhart et al. | |
| 5,340,493 A | 8/1994 | Principato | |
| 5,340,495 A | 8/1994 | Mulcahy et al. | |
| 5,350,624 A | 9/1994 | Georger et al. | |
| 5,382,400 A | 1/1995 | Pike et al. | |
| 5,389,282 A | 2/1995 | Saijo et al. | |
| 5,401,267 A | 3/1995 | Couture-Dorschner et al. | |
| 5,407,442 A | 4/1995 | Karapasha | |
| 5,415,640 A | 5/1995 | Kirby et al. | |
| 5,434,059 A | 7/1995 | Balaraman et al. | |
| 5,447,689 A | 9/1995 | Gibboni et al. | |
| 5,505,720 A | 4/1996 | Walters et al. | |
| 5,527,892 A | 6/1996 | Borsotti et al. | |
| 5,558,659 A | 9/1996 | Sherrod et al. | |
| 5,558,834 A | 9/1996 | Chu et al. | |
| 5,575,785 A | 11/1996 | Gryskiewicz et al. | |
| 5,595,754 A | 1/1997 | Ito et al. | |
| 5,607,414 A | 3/1997 | Richards et al. | |
| 5,607,760 A | 3/1997 | Roe | |
| 5,614,295 A | 3/1997 | Quincy, III et al. | |
| 5,649,916 A | 7/1997 | DiPalma et al. | |
| 5,652,148 A | 7/1997 | Doshi et al. | |
| 5,660,798 A | 8/1997 | Doshi et al. | |
| 5,695,679 A | 12/1997 | Christie et al. | |
| 5,755,710 A | 5/1998 | Menard | |
| 5,762,642 A | 6/1998 | Coles et al. | |
| 5,766,552 A | 6/1998 | Doshi et al. | |
| 5,770,543 A | 6/1998 | Garst et al. | |
| 5,785,696 A * | 7/1998 | Inoue et al. | 604/378 |
| 5,795,344 A | 8/1998 | Chappell | |
| 5,807,361 A | 9/1998 | Kajikawa et al. | |
| 5,810,798 A | 9/1998 | Finch et al. | |
| 5,883,231 A | 3/1999 | Achter et al. | |
| 5,899,893 A | 5/1999 | Dyer et al. | |
| 5,912,194 A | 6/1999 | Everhart et al. | |
| 5,961,505 A | 10/1999 | Coe et al. | |
| 6,110,158 A | 8/2000 | Kielpikowski | |
| 6,117,523 A | 9/2000 | Sugahara | |
| 6,168,654 B1 | 1/2001 | Nohr et al. | |
| 6,171,682 B1 | 1/2001 | Raidel et al. | |
| 6,172,276 B1 | 1/2001 | Hetzler et al. | |
| 6,231,719 B1 | 5/2001 | Garvey et al. | |
| 6,241,714 B1 | 6/2001 | Raidel et al. | |
| 6,322,544 B1 | 11/2001 | Laughlin et al. | |
| 6,348,253 B1 | 2/2002 | Daley et al. | |
| 6,350,711 B1 | 2/2002 | Potts et al. | |
| 6,369,293 B1 | 4/2002 | Reeves et al. | |
| 6,436,080 B1 | 8/2002 | Carlucci et al. | |
| 6,471,728 B2 | 10/2002 | Smith et al. | |
| 6,511,465 B1 | 1/2003 | Freiburger et al. | |
| 6,528,698 B2 | 3/2003 | Mizutani et al. | |
| 6,534,149 B1 | 3/2003 | Daley et al. | |
| 6,548,731 B2 | 4/2003 | Mizutani et al. | |
| 6,559,353 B1 | 5/2003 | Sheridan | |
| 6,580,015 B2 | 6/2003 | Reeves et al. | |
| 6,586,653 B2 | 7/2003 | Graeme, III et al. | |
| 6,613,028 B1 | 9/2003 | Daley et al. | |
| 6,642,430 B1 | 11/2003 | Tombult-Meyer et al. | |
| 6,657,098 B1 | 12/2003 | Niki et al. | |
| 6,663,611 B2 | 12/2003 | Blaney et al. | |
| 6,667,424 B1 * | 12/2003 | Hamilton et al. | 604/375 |
| 6,669,932 B2 | 12/2003 | Imanaka et al. | |
| 6,673,374 B2 | 1/2004 | Murad | |
| 6,673,982 B1 | 1/2004 | Chen et al. | |
| 6,677,498 B2 | 1/2004 | Chen et al. | |
| 6,696,240 B1 | 2/2004 | Kloepfer et al. | |
| 6,703,538 B2 | 3/2004 | Lassen et al. | |
| 6,730,819 B1 * | 5/2004 | Pesce | 604/360 |
| 6,812,169 B2 | 11/2004 | Potts et al. | |
| 6,838,423 B2 | 1/2005 | Irvin et al. | |
| 6,867,344 B2 | 3/2005 | Potts et al. | |
| 6,875,617 B2 | 4/2005 | Alam | |
| 6,888,044 B2 | 5/2005 | Fell et al. | |
| 6,896,669 B2 | 5/2005 | Krautkramer et al. | |
| 6,929,629 B2 | 8/2005 | Drevik et al. | |
| 6,932,929 B2 | 8/2005 | Krautkramer et al. | |
| 6,974,891 B2 | 12/2005 | Wallström | |
| 6,984,770 B2 | 1/2006 | Graeme, III et al. | |
| 7,105,715 B2 | 9/2006 | Carlucci et al. | |
| 7,160,278 B2 | 1/2007 | Mizutani et al. | |
| 7,241,627 B2 | 7/2007 | Wilhelm et al. | |
| D558,335 S | 12/2007 | Willhaus | |
| 7,316,673 B2 | 1/2008 | Drevik et al. | |
| 7,388,123 B2 | 6/2008 | Cowell et al. | |
| 7,402,157 B2 | 7/2008 | Christon et al. | |
| 7,429,689 B2 | 9/2008 | Chen et al. | |
| 7,431,715 B2 | 10/2008 | Guidotti et al. | |
| 7,431,775 B2 | 10/2008 | Wang et al. | |
| 7,504,551 B2 | 3/2009 | Herfert et al. | |
| 7,687,681 B2 | 3/2010 | Di Luccio et al. | |

(56) References Cited

U.S. PATENT DOCUMENTS

| | | | |
|---|---|---|---|
| 7,695,726 B2 | 4/2010 | Rosevear et al. | |
| 7,722,906 B2 | 5/2010 | Kandil | |
| 7,824,385 B2 | 11/2010 | Ecker et al. | |
| 7,837,944 B2 | 11/2010 | Auner et al. | |
| 7,846,281 B2 | 12/2010 | Muvundamina | |
| 7,879,744 B2 | 2/2011 | Seidling et al. | |
| 7,928,282 B2 | 4/2011 | Dibb et al. | |
| 8,029,487 B2 | 10/2011 | Bagger-Sjöbäck et al. | |
| 8,211,078 B2 | 7/2012 | Noel | |
| 8,241,915 B2 | 8/2012 | Adamczyk et al. | |
| 8,251,965 B2 | 8/2012 | Costea et al. | |
| 8,283,515 B2 | 10/2012 | Lagerstedt-Eidrup et al. | |
| 8,298,520 B2 | 10/2012 | Itoi et al. | |
| 8,367,013 B2 | 2/2013 | Kaylor et al. | |
| 8,461,411 B2 | 6/2013 | Digiacomantonio et al. | |
| 8,461,412 B2 | 6/2013 | Febo et al. | |
| 8,569,221 B2 | 10/2013 | Cunningham et al. | |
| 8,847,002 B2 | 9/2014 | Goh et al. | |
| 2002/0022813 A1 | 2/2002 | Bewick-Sonntag | |
| 2002/0082571 A1 | 6/2002 | Krivan et al. | |
| 2002/0120242 A1 | 8/2002 | Tyrrell et al. | |
| 2003/0100877 A1 | 5/2003 | Erdman | |
| 2003/0114818 A1 | 6/2003 | Benecke et al. | |
| 2003/0124336 A1 | 7/2003 | Keane et al. | |
| 2003/0130631 A1 | 7/2003 | Springer et al. | |
| 2003/0162681 A1 | 8/2003 | Hage et al. | |
| 2004/0015145 A1 | 1/2004 | Miura et al. | |
| 2004/0022678 A1 | 2/2004 | Komagoe et al. | |
| 2004/0060112 A1 | 4/2004 | Fell et al. | |
| 2005/0148488 A1 | 7/2005 | Jekel et al. | |
| 2005/0256022 A1 | 11/2005 | May et al. | |
| 2006/0111266 A1 | 5/2006 | Abera et al. | |
| 2006/0127437 A1 | 6/2006 | Kennedy et al. | |
| 2006/0189817 A1 | 8/2006 | Horlacher et al. | |
| 2006/0198797 A1 | 9/2006 | Giniger | |
| 2006/0222675 A1 | 10/2006 | Sabnis et al. | |
| 2007/0027049 A1 | 2/2007 | Rigg | |
| 2007/0055210 A1 | 3/2007 | Kao | |
| 2007/0116748 A1 | 5/2007 | Isele et al. | |
| 2007/0122360 A1 | 5/2007 | Oniki et al. | |
| 2007/0197987 A1* | 8/2007 | Tsang et al. | 604/365 |
| 2008/0276379 A1 | 11/2008 | MacDonald et al. | |
| 2008/0277621 A1 | 11/2008 | MacDonald et al. | |
| 2008/0299609 A1* | 12/2008 | Kwon et al. | 435/69.1 |
| 2009/0036856 A1 | 2/2009 | Woltman et al. | |
| 2009/0047363 A1* | 2/2009 | Itoi et al. | 424/618 |
| 2009/0062172 A1 | 3/2009 | Cunningham et al. | |
| 2009/0062764 A1 | 3/2009 | MacDonald et al. | |
| 2009/0105676 A1* | 4/2009 | Brusk et al. | 604/359 |
| 2009/0156536 A1* | 6/2009 | Kim et al. | 514/44 |
| 2009/0157021 A1 | 6/2009 | Sullivan et al. | |
| 2009/0280553 A1 | 11/2009 | Mikami et al. | |
| 2009/0306615 A1 | 12/2009 | Olsson | |
| 2010/0028638 A1 | 2/2010 | Reichardt et al. | |
| 2011/0004174 A1 | 1/2011 | Carlucci et al. | |
| 2011/0251575 A1 | 10/2011 | Kuroda et al. | |
| 2011/0288514 A1 | 11/2011 | Kuroda et al. | |
| 2012/0109088 A1 | 5/2012 | Komatsu et al. | |
| 2012/0115718 A1 | 5/2012 | Nakashita et al. | |
| 2012/0141975 A1 | 6/2012 | Sato et al. | |
| 2012/0165773 A1 | 6/2012 | Nakashita et al. | |
| 2012/0215192 A1 | 8/2012 | Corbellini et al. | |
| 2012/0296303 A1 | 11/2012 | Ng et al. | |
| 2013/0012900 A1 | 1/2013 | Uda et al. | |
| 2013/0158494 A1 | 6/2013 | Ong et al. | |
| 2013/0261584 A1 | 10/2013 | Lee et al. | |
| 2013/0261585 A1 | 10/2013 | Lee | |
| 2013/0261586 A1 | 10/2013 | Lee et al. | |

FOREIGN PATENT DOCUMENTS

| | | | |
|---|---|---|---|
| EP | 0355842 A2 | 2/1990 | |
| EP | 0355842 A3 | 2/1990 | |
| EP | 0470275 A1 | 2/1992 | |
| EP | 0560630 A1 | 9/1993 | |
| EP | 1 304 804 A1 | 9/2000 | |
| EP | 1034799 A1 | 9/2000 | |
| EP | 1034801 A1 | 9/2000 | |
| EP | 1034803 A1 | 9/2000 | |
| EP | 1034804 A1 | 9/2000 | |
| EP | 1358894 A1 | 11/2003 | |
| EP | 1 295 711 B1 | 4/2006 | |
| EP | 1 356 797 B1 | 12/2006 | |
| EP | 1 159 014 B1 | 4/2007 | |
| EP | 1 842 513 A1 | 10/2007 | |
| EP | 2 269 661 B1 | 11/2012 | |
| GB | 792531 A | 3/1958 | |
| GB | 1349955 | 4/1974 | |
| GB | 2090137 A | 7/1982 | |
| GB | 2390853 A | 1/2004 | |
| JP | 03215267 A | * | 9/1991 |
| JP | 2001070339 A | * | 3/2001 |
| WO | WO9746219 A1 | 12/1997 | |
| WO | WO9810928 A1 | 3/1998 | |
| WO | WO9926588 A2 | 6/1999 | |
| WO | WO9926588 A3 | 6/1999 | |
| WO | WO0037039 A1 | 6/2000 | |
| WO | WO0051655 A1 | 9/2000 | |
| WO | WO0051656 A1 | 9/2000 | |
| WO | WO0116268 A1 | 3/2001 | |
| WO | WO03041752 A1 | 5/2003 | |
| WO | WO03052390 A1 | 6/2003 | |
| WO | WO2005107670 A2 | 11/2005 | |
| WO | WO2005107670 A3 | 11/2005 | |
| WO | WO2006062679 A2 | 6/2006 | |
| WO | WO2006062679 A3 | 6/2006 | |
| WO | WO2006117055 A1 | 11/2006 | |
| WO | WO 2007085626 A1 | * | 8/2007 |
| WO | WO 2008139340 A1 | 11/2008 | |
| WO | WO2008139341 A2 | 11/2008 | |
| WO | WO2008139341 A3 | 11/2008 | |
| WO | WO2009027856 A2 | 3/2009 | |
| WO | WO2009027856 A3 | 3/2009 | |
| WO | WO 2009062998 A1 | 5/2009 | |
| WO | WO 2009133518 A2 | 11/2009 | |
| WO | WO 2009133518 A3 | 11/2009 | |
| WO | WO 2010017158 A1 | 2/2010 | |
| WO | WO2011027295 A2 | 3/2011 | |
| WO | WO2011027295 A3 | 3/2011 | |
| WO | WO 2012074512 A1 | 6/2012 | |

OTHER PUBLICATIONS

Cacace et al. The Hofmeister series: salt and solvent effects on interfacial phenomena. Quarterly Reviews of Biophysics. Sep. 1997; 30(3):241-77.*

Article—Lindon, et al, "A Biological Menses Simulant Using a "Batch" Homogenization Process With Varying Levels of Rheological Porperties," ip.com, PICOM000198395D, Aug. 6, 2010, pp. 1-13.

Abstract of JP Patent—4184253, Nov. 19, 2008, 2 pages.

Abstract of WO Patent—WO 01/12241, Feb. 22, 2011, 1 page.

Lee et al., U.S. Appl. No. 13/851,927, filed Mar. 27, 2013, Absorbent Articles with Decolorizing Structures.

Lee, U.S. Appl. No. 13/851,932, filed Mar. 27, 2013, Absorbent Articles with Decolorizing Structures.

Lee et al., U.S. Appl. No. 13/851,941, filed Mar. 27, 2013, Absorbent Articles with Improved Stain Decolorization.

Abstract of German Patent—DE102009029194, Apr. 7, 2011, 2 pages.

Abstract of Japanese Patent—JP1186809, Jul. 26, 1989, 1 page.

Abstract of Japanese Patent—JP3172400, Jul. 25, 1991, 1 page.

Abstract of Japanese Patent—JP63134050, Jun. 6, 1988, 1 page.

Abstract of Japanese Patent—JP1213231, Aug. 28, 1989, 1 page.

Field Guide to Stains—*How to Identify and Remove Virtually Every Stain Known to Man,* Quirk Productions, Inc., 2002, pp. 199-202.

*On-the-spot cleanup,* Consumer Reports, Jun. 1998, p. 10.

*Stain Removers: Which Are Best?,* Consumer Reports, Mar. 2000, p. 52.

*Seeing Spots? Don't Rely on Quick Stain Removers,* Consumer Reports, Aug. 2006, p. 9.

(56) References Cited

OTHER PUBLICATIONS

*Pocket Guide to Digital Printing,* Frank Cost, Delmar Publishers, Albany, NY, ISBN 0-8273-7592-1, pp. 144-145.
ASTM Designation: E 1164-02—*Standard Practice for Obtaining Spectrometric Data for Object-Color Evaluation,* Aug. 2002, 8 pages.
Japanese Industrial Standard, JIS Z 8722:2000, *Methods of colour measurement—Reflecting and transmitting objects,* Revised May 20, 2000.
Search Report and Written Opinion for PCT/IB2010/053911 dated May 26, 2011, 11 pages.
Related U.S. Patent Applications.
Abstract of Korean Patent—KR-20090100645, Sep. 24, 2009 1 page.
Machine Translation of Japanese Patent—JP07028890, 4 pages.
Online encyclopedia article: "Oxidizer." Access Oct. 6, 2008, http://en.wikipedia.org/wiki/Oxidizer, 3 pages.
Online encyclopedia article: "Fatty acid," Accessed Oct. 6, 2008, http://en.wikipedia.org/wiki/Fatty_acid, 9 pages.
O'Brien et al., U.S. Appl. No. 14/038,852, filed Aug. 27, 2013, An Absorbent Article with Side Barriers and Decolorizing Agents.

\* cited by examiner

REMOVAL OF COLORED SUBSTANCES FROM AQUEOUS LIQUIDS

RELATED APPLICATIONS

The present application claims priority to German Application No. 10 2009 029 194.6, filed on Sep. 4, 2009, the contents of which are incorporated herein in their entirety by reference thereto for all purposes.

BACKGROUND OF THE INVENTION

Colored aqueous liquid stains (e.g., blood) are a consumer-related problem in that for garment-related products, conventional washing operations are not generally sufficient to remove such stains from textile materials. Further, consumers do not like to view such blood stains. For these reasons, pre-washing agents are often employed to help facilitate the removal of the stains during washing of garment-related products. In addition to overly complicating the washing process, however, these pre-washing agents are also not a viable alternative in many applications. For example, washable and disposable absorbent articles are often used to handle blood-containing fluids, such as feminine care products and wound dressings. Because these articles are often designed for one-time use, washing is not always practical. Various solutions have therefore been proposed for minimizing the visibility of the red color of blood-containing fluids in disposable absorbent articles. One such method is described in U.S. Pat. No. 6,350,711 to Potts, et al., which generally employs Pluronic® surfactants (tri-block copolymer surfactant) to agglomerate red blood cells in blood and menses. One problem with such treatment chemistries, however, is that they can sometimes interfere with other properties of the article, such as its absorption capacity. Furthermore, such treatment chemistries are also typically expensive and relatively difficult to incorporate into the absorbent article during manufacture. Consumers are interested in reducing staining on such absorbent articles so as to reduce potential leakage soiling of their non-disposable undergarments, as well as to reduce the viewability of the unsightly stains from a comfort perspective.

As such, a need currently exits for a relatively inexpensive and simple method for removing colored substances from aqueous fluids.

SUMMARY OF THE INVENTION

In accordance with one embodiment of the present invention, an absorbent article is disclosed that comprises a liquid permeable layer, a generally liquid impermeable layer, and an absorbent core disposed between the liquid permeable layer and the generally liquid impermeable layer. A decolorizing composition for altering the color of blood-containing aqueous fluids is in fluid communication with the absorbent core, the liquid permeable layer, or combinations thereof. The decolorizing composition comprises one or more inorganic salts, each of which contains a polyvalent anion and a monovalent cation.

In accordance with another embodiment of the present invention, the use of a mixture of $Na_2SO_4$ and $KH_2PO_4$ to remove colored substances from aqueous fluids is disclosed. Furthermore, an article is also disclosed that comprises an absorbent material and a hollow enclosure disposed on a surface of the absorbent material along at least one side edge thereof, wherein the hollow enclosure is filled with a mixture of $Na_2SO_4$ and $KH_2PO_4$.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
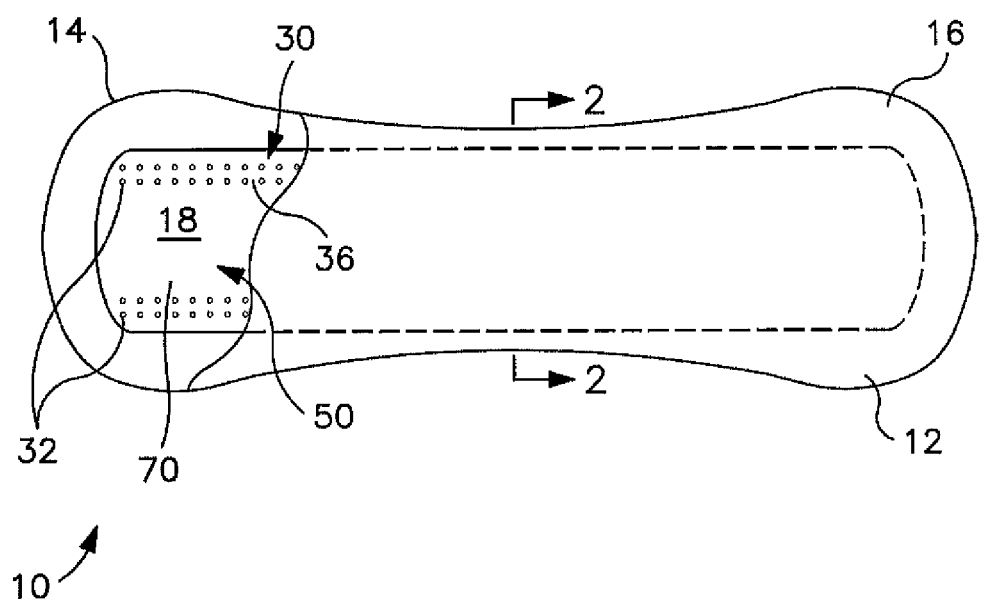
FIG. 1 is a perspective view of an absorbent article of one embodiment of the present invention.

Repeat use of references characters in the present specification and drawings is intended to represent same or analogous features or elements of the invention.

DETAILED DESCRIPTION OF REPRESENTATIVE EMBODIMENTS

Definitions

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc. The basis weight of nonwoven webs may generally vary, such as from about 5 grams per square meter ("gsm") to 150 gsm, in some embodiments from about 10 gsm to about 125 gsm, and in some embodiments, from about 25 gsm to about 120 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Geomer, et al.; which are incorporated herein in their entirety by reference thereto for all purposes.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

The present invention concerns the use of a decolorizing composition for removing colored substances from aqueous fluids (e.g., colored pigments, blood-containing fluids, etc.). More specifically, the decolorizing composition contains an inorganic salt. Without intending to be limited by theory, the present inventors believe that in aqueous fluids containing colored substances, such as red blood cells (e.g., menses, meat exudates, etc.), the inorganic salt can help agglutinate (agglomerate) the cells, thereby allowing them to be more readily separated from plasma, which is generally clear or less colored than the blood. The salt may also dissolve into the plasma to initially elevate its osmotic pressure and generate a pressure difference between the plasma and the inside of the blood cells. This causes water in the blood cells to discharge into the plasma and elevate osmotic pressure (i.e. concentration of solute) in the blood cells. As a result, the volume of blood cell decreases, which decreases the flexibility of the blood cell membrane and thereby facilitates the ability to physically separate the cells from plasma. Of course, it should be understood that the mechanism is not fully understood, and that the salt may effect the desired separation in other ways as well.

While it is desirable to enhance the ability of the red blood cells to be physically separated, it is also generally desired that inorganic salts do not induce hemolysis of the cells so that the colored hemoglobin molecules leach out of the ruptured cells to such an extent that the plasma begins to possess a color similar to the red blood cells. In this regard, the present inventors have discovered that certain types of inorganic salts are particularly effective in facilitating physical separation of red blood cells without resulting in significant cell hemolysis. More specifically, suitable inorganic salts are those containing a polyvalent anion (e.g., divalent, trivalent, etc.), such as sulfate ($SO_4^{2-}$), phosphate ($PO_4^{3-}$), carbonate ($CO_3^{2-}$), oxide ($O^{2-}$), etc., and a monovalent cation, such as sodium ($Na^+$), potassium ($K^+$), lithium ($Li^+$), ammonium ($NH_4^+$), etc. Alkali metal cations are particularly desirable. Specific examples of salts formed from such ions include, for instance, disodium sulfate ($Na_2SO_4$), dipotassium sulfate ($K_2SO_4$), disodium carbonate ($Na_2CO_3$), dipotassium carbonate ($K_2CO_3$), monosodium phosphate ($NaH_2PO_4$), disodium phosphate ($Na_2HPO_4$), monopotassium phosphate ($KH_2PO_4$), dipotassium phosphate ($K_2HPO_4$), etc. Mixtures of the aforementioned salts may be particularly effective in facilitating physical separation of red blood cells. For instance, the mixture may contain two or more salts that contain a different anion, cation, or both. The salts may retain their separate crystalline structures, or they may form a double salt having a crystalline structure different than the individual salts. In one particular embodiment, a mixture of a phosphate salt and sulfate salt is employed, with the cation being the same or different. For instance, a mixture of disodium sulfate ($Na_2SO_4$) and monopotassium phosphate ($KH_2PO_4$) may be employed. Such a salt mixture may contain 10 wt. % to 90 wt. %, especially 40 wt. % to 60 wt. %, and preferably about 50 wt. % $Na_2SO_4$, as well as 10 wt. % to 90 wt. %, especially 40 wt. % to 60 wt. %, and preferably about 50 wt. % $KH_2PO_4$.

The form of the salt in the decolorizing composition may vary as desired. In one particular embodiment, for example, the salt is employed in a solid form. When multiple solid salts are employed, it is desired that they have approximately the same particle size and distribution to avoid segregation. If desired, this can be achieved by grinding of the particles. The salt(s) typically constitute a significant portion of the decolorizing composition, such as more than 70 wt. %, in some embodiments more than 90 wt. %, and in some embodiments, from 95 wt. % to 100 wt. % of the decolorizing composition. In fact, the decolorizing composition preferably consists only of the salt(s) (e.g., $Na_2SO_4$ and $KH_2PO_4$). Nevertheless, in certain embodiment of the present invention, the decolorizing composition may also include various other components.

In one embodiment, for example, the decolorizing composition may contain a superabsorbent material to help absorb some or all of the fluid upon separation from the red blood cells (e.g., plasma). Superabsorbent materials are water-swellable materials capable of absorbing at least about 20 times their weight and, in some cases, at least about 30 times their weight in an aqueous solution containing 0.9 weight percent sodium chloride. The superabsorbent material may, for example, include natural and/or synthetic polymers. Examples of synthetic superabsorbent material polymers may include alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Other superabsorbent materials may include hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum and so forth. Particularly suitable superabsorbent polymers are HYSORB 8800AD (BASF of Charlotte, N.C. and FAVOR SXM 9300 (available from Degussa Superabsorber of Greensboro, N.C.). When employed, the superabsorbent material typically constitutes no more than about 50 wt. %, and in some embodiments, from about 0.5 wt. % to about 20 wt. % of the decolorizing composition.

Regardless of its particular constituents, the decolorizing composition of the present invention may also be disposed on a substrate that contain pores which help facilitate the separation of the colored substance (e.g., red blood cells) from the aqueous fluid. The substrate may also help absorb the aqueous fluid, particularly those components of the fluid (e.g., plasma) that are separated from the colored substance. Due to charge and hydrophilicity/hydrophobicity affinity, the aqueous fluid may also adhere well to the substrate. The substrate may be formed from a variety of different materials, such as woven fabric, knit fabric, perforated plastic film, plastic net, foam, nonwoven fabric or a laminate of two or more layers of such material. Suitable nonwoven fabrics can include natural fibers (e.g., cellulose, fluff pulp, cotton, cotton, wool, peat, etc.) and/or synthetic fibers such as polyethylene, polypropylene, polyester, polyurethane, nylon or regenerated cellulose fibers. It is also possible to use substrates made of fibers with two or more components, and mixtures different types of fibers. In certain embodiments, the substrate is formed from an absorbent material (e.g., cellulosic fibers or web) that is able to absorb some or all of the fluid upon separation from the red blood cells (e.g., plasma). The substrate may also contain other components, such as binders, heated treated thermoplastic fibers, foam, etc.

The substrate may include a single layer or it may contain multiple layers. Further, the shape of the substrate may vary as desired, such as round, oval, square, rectangular, trapezoidal or hourglass-shaped, that is, a narrower central section and wider having end sections, or any irregularly shaped flat object. The substrate may be in the form of rolls, bundles, sheets, etc. In one particular embodiment, for example, the substrate is a hollow enclosure within which the decolorizing composition is disposed so that it is sufficiently retained prior to use. The enclosure may be formed from a variety of materials as described above, such as a woven or knit fabric, film, nonwoven web, foam, laminates thereof, and so forth. The hollow enclosure may have a variety of different shapes, such as a tube (e.g., ring-shaped tube). In certain embodiments, the hollow enclosure is disposed adjacent to an absorbent material that is capable of absorbing the aqueous fluid or a component thereof. If desired, the hollow enclosure may be disposed along one or more edges of the absorbent material so that, even if the aqueous fluid is not absorbed by the material, the enclosure can still inhibit leakage of the colored substance therefrom.

The manner in which the decolorizing composition is applied to the substrate may depend in part on the nature of the composition and substrate. For example, the decolorizing composition may be applied in a solid form by simply admixing it with the constituents used to form the substrate. In one embodiment, the decolorizing composition may be entrained into cellulosic fibers during their formation into a web structure. Likewise, an adhesive may be used to help bind the composition to the substrate. Suitable adhesives include known hot melt adhesives, pressure sensitive adhesives, etc. In still other embodiments, the decolorizing composition is applied to the substrate in the form of a coating solution. Various solvents may be employed to form the solution, such as water; alcohols such as ethanol or methanol; dimethylformamide; dimethyl sulfoxide; hydrocarbons such as pentane, butane, heptane, hexane, etc.; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. The resulting coating solution may be applied to the substrate using various techniques, such as printing, bar, roll, knife, curtain, spray, slot-die, dip-coating, drop-coating, extrusion, stencil application, etc. The solvent(s) may constitute from about 10 wt. % to about 80 wt. %, in some embodiments from about 20 wt. % to about 70 wt. %, and in some embodiments, from about 40 wt. % to about 60 wt. % of the solution. Once applied, the solution may then be dried to remove some or all of the solvents from the solution.

The relative dry add-on level of the decolorizing composition may vary to achieve the desired level of decolorization. The "add-on level" is determined by subtracting the weight of the untreated substrate from the weight of the treated substrate (after any optional drying steps), dividing this calculated weight by the weight of the untreated substrate, and then multiplying by 100%. One particular benefit of the present invention is that relatively high add-on levels may be achieved to facilitate color removal without adversely impacting other functions of the substrate (e.g., absorbency). In some embodiments, for example, the add-on level of the decolorizing composition may be about 50% or more, in some embodiments from about 100% to about 2500%, and in some embodiments, from about 250% to about 2000%. The decolorizing composition may likewise be employed in an amount from 0.1 to 1 gram per milliliter of the aqueous fluid with which it is contacted.

The treated substrate is used to remove colored substances from a wide variety of different aqueous fluids. In one particular embodiment, for example, the treated substrate is incorporated into a disposable absorbent article to help minimize the leakage of colored blood cells from bodily exudates (e.g., menses, blood, etc.). The disposable absorbent article may be a diaper, training pant, absorbent underpants, incontinence article, feminine hygiene product (e.g., sanitary napkin), swim wear, baby wipe, and so forth; medical absorbent article, such as garment, fenestration material, underpad, bedpad, absorbent drape, and medical wipe; food service wiper; food collection pad (e.g., meat pad); clothing article; and so forth. The treated substrate may be employed in any part or layer of the absorbent article, so long as it is capable of contacting the target aqueous fluid (e.g., blood, menses, etc.). In this regard, various embodiments of an absorbent article that may be formed according to the present invention will now be described in more detail.

Figure 2:
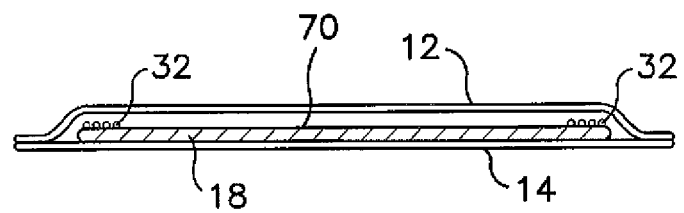
FIG. 2 is a cross-sectional view of the absorbent article of FIG. 1 taken along the lines indicated in FIG. 1.

Referring to FIGS. 1-2, for example, one embodiment of an absorbent article 10 is shown that includes a generally liquid permeable topsheet 12, a generally liquid impermeable backsheet 14, and an absorbent core 18 disposed between the topsheet 12 and backsheet 14. The topsheet 12 may surround the absorbent core 18 so that it completely encases the absorbent article 10. Alternatively, the topsheet 12 and the backsheet 14 may extend beyond the absorbent core 18 and be peripherally joined together, either entirely or partially, using known techniques. Typically, the topsheet 12 and the backsheet 14 are joined by adhesive bonding, ultrasonic bonding, or any other suitable joining method known in the art, the sealed edges defining an overall sealed peripheral edge 16 of the article 10. The article 10 may take on various geometries but will generally have opposite lateral sides and longitudinal ends.

The topsheet 12 is generally designed to contact the body of the user and is liquid-permeable. The liquid permeable topsheet 12 has an outwardly facing surface that may contact the body of the wearer and receive aqueous fluids from the body. The topsheet 12 is provided for comfort and conformability and functions to direct bodily exudates away from the body, through the topsheet 12 and toward the absorbent core 18. The topsheet 12 retains little or no liquid in its structure so that it provides a relatively comfortable and non-irritating surface next to the tissues within the vestibule of a female wearer. The topsheet 12 can be constructed of any woven or nonwoven material which is easily penetrated by bodily exudates which contact the surface of the backsheet. Examples of suitable materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable topsheet material is a bonded carded web made of polypropylene and polyethylene such as that used as topsheet stock for KOTEX® pantiliners and obtainable from Sandler Corporation, Germany. U.S. Pat. No. 4,801,494 to Datta, et al. and U.S. Pat. No. 4,908,026 to Sukiennik, et al. teach various other topsheet materials that may be used in the present invention.

The topsheet 12 may also contain a plurality of apertures (not shown) formed therethrough to permit body fluid to pass more readily into the absorbent core 18. The apertures may be randomly or uniformly arranged throughout the topsheet 12, or they may be located only in the narrow longitudinal band or strip arranged along the longitudinal axis of the absorbent article 10. The apertures permit rapid penetration of body fluid down into the absorbent core 18. The size, shape, diameter and number of apertures may be varied to suit one's particular needs. The topsheet 12 may also be embossed with any desired embossing pattern to define embossed channels. Embossing techniques are well known to those skilled in the art. An embossing pattern not only creates an aesthetically pleasing surface, the channels facilitate intake of menses fluid. Menses will tend to flow along the densified edges of the channels rather than pool on contact points of the topsheet 12.

As stated above, the absorbent article 10 also includes a backsheet 14. The backsheet 14 is generally liquid-impermeable and designed to face the inner surface, i.e., the crotch portion of an undergarment (not shown). The backsheet 14 may permit a passage of air or vapor out of the absorbent article 10, while still blocking the passage of liquids. Any liquid-impermeable material may generally be utilized to form the backsheet 14. For example, one suitable material that may be utilized is a microporous polymeric film, such as polyethylene or polypropylene. In particular embodiments, a polyethylene film is utilized that has a thickness in the range of about 0.2 mils to about 5.0 mils, and particularly between about 0.5 to about 3.0 mils. A specific example of a backsheet material is a polyethylene film such as that used in KOTEX® pantiliners and obtainable from Pliant Corporation, Schaumburg, Ill., USA.

The absorbent article 10 also contains an absorbent core 18 positioned between the topsheet 12 and the backsheet 14 that provides capacity to absorb and retain bodily exudates. The absorbent core 18 may be selected so that it possesses a particular individual total absorbency depending on the intended article of use. For example, for infant care products, the total absorbency can be within the range of about 200-900 grams of 0.9 wt % saline, and can typically be about 500 grams of saline. For adult care products, the total absorbency can be within the range of about 400-2000 grams of saline, and can typically be about 1300 grams of saline. For feminine care products, the total absorbency can be within the range of about 7-50 grams of menstrual fluid, and can typically be within the range of about 30-40 g of menstrual fluid.

The absorbent core 18 may be formed from a variety of different materials and contain any number of desired layers. For example, the core 18 typically includes one or more layers of an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material includes a matrix of cellulosic fluff, and may also include superabsorbent material. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

The absorbent article 10 may also contain additional layers. For example, in one embodiment, the absorbent article may contain a liquid-permeable transfer delay layer (not shown) positioned vertically below the topsheet. The transfer delay layer may contain a material that is substantially hydrophobic. For example, the transfer delay layer may be a nonwoven fibrous web composed of a relatively hydrophobic material, such as polypropylene, polyethylene, polyester or the like, and also may be composed of a blend of such materials. One example of a material suitable for the transfer delay layer is a spunbond web composed of polypropylene, multi-lobal fibers. Further examples of suitable transfer delay layer materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al. To adjust the performance of the invention, the transfer delay layer may also be treated with a selected amount of surfactant to increase its initial wettability. The transfer delay layer may generally have any size, such as a length of about 150 mm to about 300 mm. Typically, the length of the transfer delay layer is approximately equal to the length of the absorbent article 10. The transfer delay layer may also be equal in width to the intake layer, but is typically wider. For example, the width of the transfer delay layer may be from between about 50 mm to about 75 mm, and particularly about 48 mm. The transfer delay layer typically has a basis weight less than that of the other absorbent members. For example, the basis weight of the transfer delay layer is typically less than about 250 grams per square meter (gsm), and in some embodiments, between about 40 gsm to about 200 gsm.

The absorbent article 10 may also contain a liquid-permeable intake layer (not shown) positioned between the topsheet 12 and optional transfer delay layer (not shown). The intake layer may be made of a material that is capable of rapidly transferring, in the z-direction, body fluid that is delivered to the topsheet 12. The intake layer may generally have any shape and/or size desired. In one embodiment, the intake layer has a rectangular shape, with a length equal to or less than the overall length of the absorbent article 10, and a width less than the width of the absorbent article 10. For example, a length of between about 150 mm to about 300 mm and a width of between about 10 mm to about 60 mm may be utilized. Any of a variety of different materials are capable of being used for the intake layer to accomplish the above-mentioned functions. The material may be synthetic, cellulosic, or a combination of synthetic and cellulosic materials. For example, airlaid cellulosic tissues may be suitable for use in the intake layer. The airlaid cellulosic tissue may have a basis weight ranging from about 10 grams per square meter (gsm) to about 300 gsm, and in some embodiments, between about 40 gsm to about 150 gsm. The airlaid tissue may be formed from hardwood and/or softwood fibers. The airlaid tissue has a fine pore structure and provides an excellent wicking capacity, especially for menses.

The decolorizing composition of the present invention may generally be applied to any liquid-permeable layer of the absorbent article 10 where it can contact aqueous fluids exuded by the body (e.g., menses), such as the absorbent core 18, topsheet 12, intake layer (not shown), transfer delay layer (not shown), and so forth. In FIGS. 1-2, for instance, the decolorizing composition 32 is disposed directly on a body-facing surface 70 of the absorbent core 18. Of course, it should also be understood that the decolorizing composition may also be disposed on an interior surface (facing the backsheet 14).

The decolorizing composition may be applied continuously or discontinuously over some or all of a surface of a liquid-permeable layer (e.g., absorbent core, intake layer, transfer layer, etc.). In one embodiment, the decolorizing composition may cover only a portion of the surface to ensure that the layer is still capable of retaining sufficient absorbent properties. For example, the decolorizing composition may be present within at least one boundary zone (e.g., two) located at or near the periphery of the layer. In this manner, the decolorizing composition may help discharge color at the edges of the article where leakage is most likely to occur. At least one interior zone may also be present adjacent to the boundary zone that constitutes from about 5% to about 90%, in some embodiments from about 10% to about 85%, and in some embodiments, from about 15% to about 75% of the surface area of the layer. The interior zone may be left substantially untreated with the decolorizing composition to enable a user to observe and inspect the bodily exudates for infection or other health related conditions, and also allows the decolorizing composition to be applied only to those portions of the layer needed to achieve the desired effect so that the untreated zone can continue to fulfill its other functions, such as absorbing or wicking fluids, etc. Referring again to FIG. 1, for example, two boundary zones 30 are shown that are defined in a longitudinally extending pattern along opposite lateral sides of a longitudinal centerline of the article 10. At least a portion of each boundary zone 30 has a laterally inboard dimension 36 overlying a longitudinally extending periphery portion of the underlying absorbent core 18. As illustrated, the boundary zones 30 may extend laterally outward to an edge of the absorbent core 18 to help decolorize bodily exudates at the areas in which they are most likely to leak from the article. A longitudinally extending interior zone 50 is also defined on the absorbent core 18 between the opposing boundary zones 30, at least a portion of which is left substantially untreated with the decolorizing composition so that a user is able to monitor the bodily exudates for infection or other health-related conditions. The shapes of the boundary zones may vary as desired. In the embodiment illustrated in FIG. 1, for example, each of the two longitudinally extending boundary zones 30 is defined by a stripe extending longitudinally on opposite sides of a centerline axis of the article 10. Multiple stripes may also be employed. Likewise, the zones 30 also need not extend the entire length of the absorbent core 18. Any other suitable zone pattern may be employed in the present invention.

Figure 3:
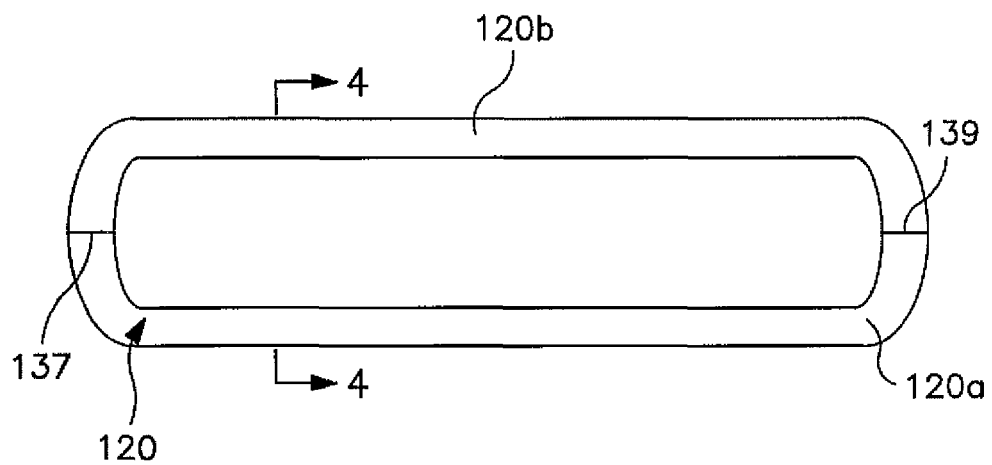
FIG. 3 is a perspective of an absorbent article of another embodiment of the present invention.
Figure 4:
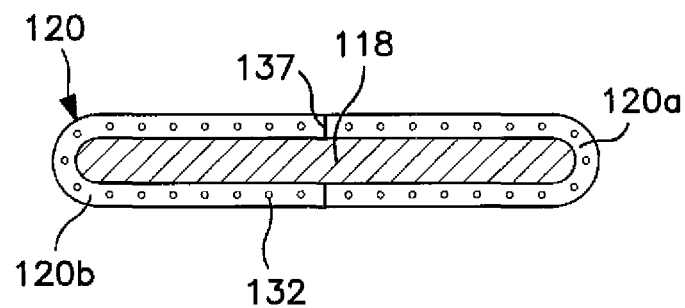
FIG. 4 is a cross-sectional view of the absorbent article of FIG. 3 taken along the lines indicated in FIG. 3.

In addition to being coated directly on the absorbent core, such as shown in FIGS. 1-2, other configurations may also be employed in the present invention. Referring to FIGS. 3-4, for example, another embodiment of an absorbent core 118 is shown that may be employed in an absorbent article such as described above. An additional layer 120 is placed in contact with the absorbent core 118. The layer 120 may be formed from a variety of different porous materials, such as a perforated film, nonwoven web (e.g., cellulosic web, spunbond web, meltblown web, etc.), foams, etc. In the illustrated embodiment, the layer 120 is in the form of a hollow enclosure (e.g., sachet, bag, etc.) that is folded so that it partially or completely surrounds the absorbent core 118. A decolorizing composition 132 may be disposed within the layer 120 so that it remains sealed therein prior to use. The layer 120 is shown as being formed from two separate components 120a and 120b that are sealed together at seams 137 and 139, respectively. It should be understood, however, that a single component may also be employed.

Figure 5:
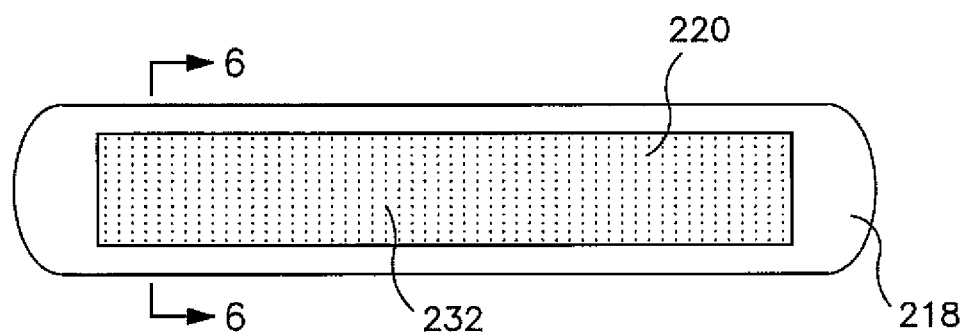
FIG. 5 is a perspective of an absorbent article of yet another embodiment of the present invention.
Figure 6:
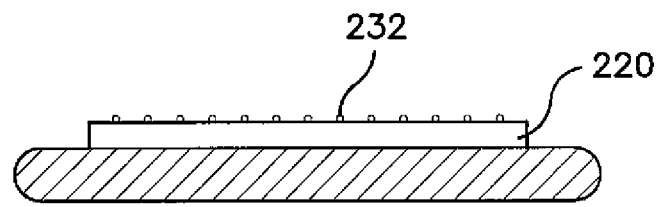
FIG. 6 is a cross-sectional view of the absorbent article of FIG. 5 taken along the lines indicated in FIG. 5.

An alternative embodiment of an absorbent core 218 is shown in FIGS. 5-6. In this particular embodiment, an additional layer 220 is laminated to the absorbent core 218. Although not shown, an adhesive (e.g., pressure-sensitive, hot melt, etc.) may be employed to ensure that the layer 220 is sufficiently adhered to the absorbent core 218. A decolorizing composition 232 is also disposed on the layer 220 in a manner such as described above. In the illustrated embodiment, the decolorizing composition 232 is disposed on a surface facing away from the absorbent core 218; however, it should also be understood that the decolorizing composition 232 may be positioned on any other surface, such as between the layer 220 and the absorbent core 218.

Although the decolorizing composition has been described in detail above with respect to its use on a disposable absorbent article, it should be understood that the present invention is by no means limited to such embodiments. For example, the decolorizing composition may also be used to remove a colored substance from a textile fabric (e.g., clothing, woven cloth, etc.) to result in an unstained aqueous liquid or at most a colorless stain. Such colorless soils do not need to be pretreated immediately, but can simply be washed during the normal washing cycle. Other materials that may also be treated with the decolorizing composition, such as a packaging material (e.g., under a packaged piece of an absorption fabric for meats, often called a "meat pad"). Such meat pads often have one or more liquid-permeable and absorbent materials or layers attached to a generally liquid impermeable back layer. The absorbent layer is typically located adjacent to the meat. It is envisioned that such decolorizing materials could be incorporated in or on any layer within the meat pad, but desirably away from contact with the meat.

It should also be understood that the manner in which the colored substance is removed from an aqueous liquid using the decolorizing composition of the present invention may vary. In certain embodiments, for example, the decolorizing composition may simply be added to a stained aqueous fluid. It is advantageous, however, that the aqueous fluid is allowed to pass through the decolorizing composition so that it can physically separate the colored substance, leaving a liquid having a lighter color (e.g., clear or yellow). This may be accomplished through the application of pressure (e.g., by sucking or pressing), capillary action, etc. Preferably, contact between the aqueous fluid and decolorizing composition occurs relatively quickly so that the inorganic salts do not dissolve in the fluid.

The present invention may be better understood with reference to the following examples.

EXAMPLE 1

A sachet of non-woven material with dimensions of 6×0.5 cm was filled with 0.5 grams of a mixture of $Na_2SO_4$ and $KH_2PO_4$ (weight ratio of 1:1) and the filling aperture was sewn up or bonded together. Two of the filled sachets were inserted into a sheet-like down material in such a way that they were positioned longitudinally parallel to one another. Centrally between the two sachets, 2.5 milliliters of sheep's blood was applied and pressed through the sachets. The blood underwent separation into colorless plasma, which emerged through the sachets. The red blood corpuscles were retained by the sachets.

EXAMPLE 2

The ability to form an absorbent article with the decolorizing composition of the present invention was demonstrated. Initially, two airlaid substrates (60 gsm, 17 cm×1.5 cm) were each soaked with a 45% solution of $Na_2SO_4$ and $KH_2PO_4$ (weight ratio of 1:1) and dried in an oven. 1.2 grams of the salt mixture (dry weight) was loaded per substrate. The treated substrates were then placed in communication with an absorbent core that contained two layers—(1) an airlaid layer having an hourglass shape and a basis weight of 60 gsm and (2) a fluff/superabsorbent layer having a basis weight of 146 gsm. The treated substrates were positioned on opposing sides of the airlaid layer. A transfer delay layer (apertured, bonded carded laminate having a basis weight of 168 gsm) was also located adjacent to the top (body facing side) of the airlaid layer and between the salt-treated substrates. The absorbent article also contained a backsheet and topsheet, which were formed from materials such as described above. The resulting article was applied with a swine blood simulant (1-3 milliliters). The treated side of the article remained generally clear.

EXAMPLE 3

An absorbent article was formed in a manner similar to that described in Example 2, except that the airlaid layer of the absorbent core was directly treated with the salt mixture. More particularly, the salt mixture was coated onto opposing sides of the airlaid layer to form two separate coating zones, each having a dimension of 17 cm×1 cm. Each zone contained 2 grams of the salt mixture (dry weight). A hydrophobic/hydrophilic spunbond web (25 gsm) was then disposed over the salt mixture and attached thereto using a construction adhesive (National Starch 5210U). The resulting article was applied with a swine blood simulant (3 milliliters). The treated side of the article remained generally clear as compared to a control article (without the salt treatment), which yielded a red rewet.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article, comprising:
a liquid permeable layer;
a generally liquid impermeable layer;
an absorbent core disposed between the liquid permeable layer and the generally liquid impermeable layer; and
a decolorizing composition for altering the color of blood-containing aqueous fluids, wherein the decolorizing composition is in fluid communication with the absorbent core, the liquid permeable layer, or combinations thereof, wherein the decolorizing composition comprises a first inorganic salt, and a second inorganic salt, wherein the first inorganic salt and the second inorganic salt each contain a polyvalent anion and a monovalent cation, wherein the decolorizing composition consists essentially of the inorganic salts, wherein the decolorizing composition contained within a hollow enclosure, wherein the hollow enclosure is formed from a fibrous web, further wherein the hollow enclosure completely surrounds the absorbent core.

2. The absorbent article of claim 1, wherein each polyvalent anion is a sulfate, phosphate, carbonate.

3. The absorbent article of claim 1, wherein each monovalent cation is sodium, lithium, potassium, ammonium.

4. The absorbent article of claim 1, wherein the inorganic salts are in solid form.

5. The absorbent article of any of claim 1, wherein the decolorizing composition further comprises a superabsorbent material.

6. The absorbent article of claim 1, wherein the article is a sanitary napkin.

7. The absorbent article of claim 1, wherein the absorbent article is a meat pad.

8. An absorbent article, comprising;
a liquid permeable layer;
a generally liquid impermeable layer;
an absorbent core disposed between the liquid permeable layer and the generally liquid impermeable layer; and
a decolorizing composition for altering the color of blood-containing aqueous fluids, wherein the decolorizing composition is in fluid communication with the absorbent core, the liquid permeable layer, or combinations thereof, wherein the decolorizing composition comprises a first inorganic salt and a second inorganic salt, wherein the first inorganic salt and the second inorganic salt each contain a polyvalent anion and a monovalent cation, wherein the-decolorizing composition comprises monopotassium phosphate and sodium sulfate, wherein the decolorizing composition contains from about 40 wt. % to about 60 wt. % of monopotassium phosphate and from about 40 wt. % to about 60 wt. % of sodium sulfate, wherein the decolorizing composition is contained within a hollow enclosure, wherein the hollow enclosure is formed from a fibrous web, further wherein the hollow enclosure completely surrounds the absorbent core.

* * * * *

UNITED STATES PATENT AND TRADEMARK OFFICE
CERTIFICATE OF CORRECTION

PATENT NO. : 9,161,868 B2
APPLICATION NO. : 13/387157
DATED : October 20, 2015
INVENTOR(S) : Corbellini et al.

Page 1 of 1

It is certified that error appears in the above-identified patent and that said Letters Patent is hereby corrected as shown below:

In the claims

Column 12, line 28-29, claim 2

"The absorbent article of claim 1, wherein each polyvalent anion is a sulfate, phosphate, carbonate." should read --The absorbent article of claim 1, wherein each polyvalent anion is a sulfate, phosphate, or carbonate.--

Column 12, line 30-31, claim 3

"The absorbent article of claim 1, wherein each monovalent cation is sodium, lithium, potassium, ammonium." should read --The absorbent article of claim 1, wherein each monovalent cation is sodium, lithium, potassium, or ammonium.--

Signed and Sealed this
Twenty-first Day of June, 2016

Michelle K. Lee
*Director of the United States Patent and Trademark Office*